(12) United States Patent
Rees et al.

(10) Patent No.: US 8,569,451 B2
(45) Date of Patent: Oct. 29, 2013

(54) AFFINITY MATERIAL (75) Inventors: Anthony Rees, Uppsala (SE); Börje Sellergren, Schwerte (DE); Ecevit Yilmaz, Bjärred (SE); Thomas Schrader, Mettmann (DE)

(73) Assignee: Biotage AB (SE)

( * ) Notice: Subject to any disclaimer, the term of this patent is extended or adjusted under 35 U.S.C. 154(b) by 0 days.

(21) Appl. No.: 13/263,954

(22) PCT Filed: Apr. 9, 2010

(86) PCT No.: PCT/EP2010/054681
§ 371 (c)(1),
(2), (4) Date: Dec. 30, 2011

(87) PCT Pub. No.: WO2010/118985
PCT Pub. Date: Oct. 21, 2010

(65) Prior Publication Data
US 2012/0095165 A1    Apr. 19, 2012

(30) Foreign Application Priority Data

Apr. 15, 2009 (SE) ...................................... 0900499

(51) Int. Cl.
*C07K 17/00* (2006.01)
(52) U.S. Cl.
USPC .... 530/328; 435/7.1; 526/238.2; 526/238.22; 526/265; 526/268; 526/303.1; 526/306; 530/329; 530/330; 530/331
(58) Field of Classification Search
USPC .......... 435/7.1; 526/238.2, 238.22, 265, 268, 526/278, 303.1, 306; 530/328, 329, 330, 530/331
See application file for complete search history.

(56) References Cited

U.S. PATENT DOCUMENTS

2003/0049870 A1    3/2003    Glad et al.

FOREIGN PATENT DOCUMENTS

| WO | WO-93/05068 A1 | 3/1993 |
| WO | WO-01/32760 A1 | 5/2001 |
| WO | WO-2006/004536 A1 | 1/2006 |
| WO | WO-2007/146968 A2 | 12/2007 |

OTHER PUBLICATIONS

Titirici, M.-M., "Synthesis and Evaluation of Novel Formats in Molecular Imprinting", Ph.D Thesis, University of Mainz and Dortmund, Germany, (Jan. 2005), 233 pgs.
"International Application Serial No. PCT/EP2010/054681, International Search Report mailed Aug. 12, 2010", 4 pgs.
"International Application Serial No. PCT/EP2010/054681, Written Opinion mailed Aug. 12, 2010", 4 pgs.
Hart, B. R., et al., "Molecular Imprinting for the Recognition of N-Terminal Histidine Peptides in Aqueous Solution", *Macromolecules*, 35(16), (2002), 6192-6201.
Presta, L. G., et al., "Molecular engineering and design of therapeutic antibodies", *Curr. Opin. Immunol.*, 20(4), (2008), 460-470.
Rachkov, A., et al., "Towards molecularly imprinted polymers selective to peptides and proteins. The epitope approach", *Biochimica et Biophysica Acta*, 1544, (2001), 255-266.
Renner, C., et al., "Arginine- and Lysine-Specific Polymers for Protein Recognition and Immobilization", *J. Am. Chem. Soc.*, 128(2), (2006), 620-628.
Serizawa, T., et al., "Peptide Motifs That Recognize Differences in Polymer-Film Surfaces", *Angewandte Chemie. International Edition*, 46(5), (2007), 723-726.
Steinke, J. H. G., et al., "A simple polymerisable carboxylic acid receptor: 2-acrylamido pyridine", *Trends in Analytical Chemistry*, 18(3), (1999), 159-164.
Sun, W., et al., "A Fluorescent Polymer Heparin Sensor", *Chemistry—A European Journal*, 13(27), (2007), 7701-7707.
Taden, A., et al., "Synthesis and Polymerization of 5-(Methacrylamido)tetrazole, a Water-Soluble Acidic Monomer", *Journal of Polymer Science Part A: Polymer Chemistry*, 40(23), (2002), 4333-4343.

Primary Examiner — Robert Jones, Jr.
(74) Attorney, Agent, or Firm — Schwegman Lundberg & Woessner, P.A.

(57) ABSTRACT

The present application relates to an affinity material useful in antibody purification.

12 Claims, 2 Drawing Sheets

¹EPQV YTLP PSRD ELTK NQVS LTCL VKGF YPXX SDIA VEWE
⁴¹SNGQ PENN YKTT PPVL DSDG SFFL YSKL TV<u>DK SRWQ</u> QGNV
⁸¹FSCS VMHE AXLH NHYT <u>QKSL SLSP GK</u>

AFFINITY MATERIAL

RELATED APPLICATIONS

This application is a nationalization under 35 U.S.C. 371 of PCT/EP2010/054681, filed Apr. 9, 2010 and published as WO 2010/118985 A1 on Oct. 21, 2010, which claims priority to Sweden Patent Application No. 0900499-5, filed Apr. 15, 2009; which applications and publications are incorporated herein by reference in their entirety.

BACKGROUND OF THE INVENTION

Antibodies as therapeutics is one of the most rapidly growing segments of biopharmaceuticals in which proteins are used as active pharmaceutical ingredients. The antibody field of research and development is broad and includes the use of full length antibodies (Ab), single chain variable region fragments (scFv), single domain antibodies (dAb) and other multi-functional constructions (eg diabodies etc) (Presta, L G. *Curr. Opin. Immunol.* 2008, 20:460-470). The main disease targets for antibody therapies are cancer, autoimmune diseases, cardiac diseases and infectious diseases.

One of the major challenges of antibody production is faced during work-up after fermentation which may use eukaryotic (yeasts, plants or mammalian) or prokaryotic (bacteria) expression vehicles depending on the type of antibody construct under study. Numerous costly purification steps have to be employed in order to reach the required purity levels. These often consist of combinations of two or more different separation techniques (Satinder Ahuja (Ed.), Handbook of Bioseparations in Separation Science and Technology (Vol. 2). Academic Press, San Diego Calif., 2000) aiming at removing impurities to reach an acceptable purity level. A typical process would involve:

Cell culture harvest
|
Protein A affinity chromatography
|
Physicochemical inactivation (eg low pH 'hold')
|
Additional orthogonal chromatography step(s)
|
Nanofiltration
|
Final filtration and formulation So far no single separation technique capable of taking crude antibody through to late stage filtration exists. As shown above, the downstream process is commonly divided into a capturing and separation step and a various polishing steps, each with their different requirements on the respective separation materials. Conventionally the choice of separation technique used depends on cost, binding capacity and reusability.

Figure 1:
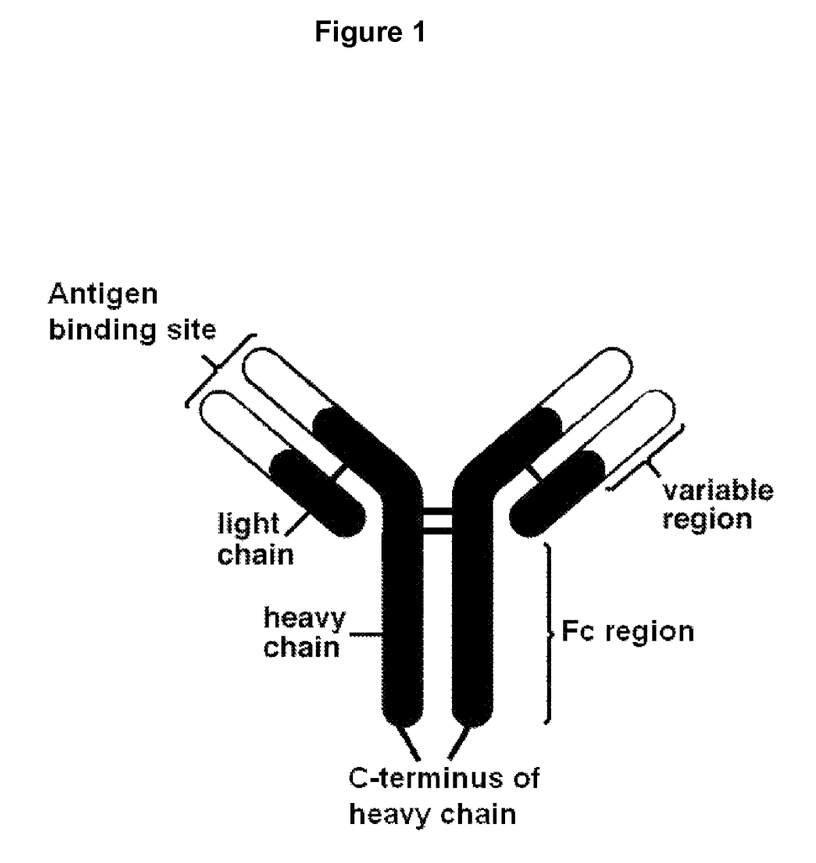
FIG. 1 discloses a general schematic figure of Immunglubulin G. The constant regions are disclosed in black.

The capturing and initial separation step is typically based on affinity materials such as protein A, small ligands, aptamers etc. The most commonly used affinity material is protein A attached to a solid support such as agarose, silica or dextran. Protein A is a relatively robust 42 kD protein exhibiting affinity for the Fc region (heavy chain) of IgG (Immunoglobulin G)—see FIG. 1. While commonly used, Protein A materials are expensive, may result in column bleeding and consequential toxicity problems if not removed and may undergo denaturation during regeneration which typically involves high pH cycling. They are also susceptible to protease digestion and concomitant loss of function.

Alternative, less selective chemical materials can be used such as those based on thiophilic, boronate, immobilized metal ion chromatography (IMAC) or hydrophobic interaction chromatography (HIC) principles. All these methods suffer from different drawbacks (requirement of additional, non-native amino acids to be present at the C-terminus of the antibody chain (eg oligo-histidine for IMAC), leakage, need for high salt, low selectivity etc) which have precluded their widespread use at the process scale level. Recent improvements however, have been achieved by combining two separation principles in a single ligand incorporating ion-exchange and thiophilic separation principles.

For the intermediate/polishing purification steps either multi-modal anion exchange resins with or without further anion or cation exchanger steps may be employed (eg Capto Adhere, CaptoQ or CaptoS from GE Healthcare). While such steps are currently necessary the sum total adds up to 3 to 4 different stages of purification each of which will contribute to antibody losses and each of which needs to fulfill the regulatory (eg FDA) requirements of being stable to alkaline regeneration without leakage of components into the antibody preparation.

Product Polishing describes the final processing steps which end with packaging of the product in a form that is stable, easily transportable and convenient. Crystallization, desiccation, lyophilization and spray drying are typical unit operations. Depending on the product and its intended use, polishing may also include operations to sterilize the product and remove or deactivate trace contaminants which might compromise product safety. Such operations might include the removal of viruses or depyrogenation.

US2003049870 mentions that molecularly imprinted polymers may be prepared using entire antibodies as templates. The potential advantages of MIPs used in this way are however severely compromised where the template (an antibody) is the same molecule as the therapeutic product (viz the antibody). Further, an intact antibody as a template is expensive to produce and adds significant cost to the MIP thereby making it less competitive than existing methods (eg Protein A). It is also liable to retention in the polymer and hence leakage during use.

SUMMARY OF THE INVENTION

One object of the present invention is to provide an affinity material useful in antibody purification.

One object of the present invention is to provide an affinity material useful in downstream processing in antibody production.

One object of the present invention is to provide an affinity material useful in the capture step in downstream processing in antibody production.

One object of the present invention is to prepare methods for purification of antibodies.

One object of the present invention is to provide a material replacing the material conventionally used in one or more of the conventionally used capturing, separation and polishing steps in downstream processing in antibody production.

One object of the present invention is to provide a method for antibody purification replacing one or more of the conventionally used capturing, separation and polishing steps in downstream processing in antibody production.

One object of the present invention is to provide a method for antibody purification replacing two or more of the con- ventionally used capturing, separation and polishing steps in downstream processing in antibody production by one single step.

One object of the present invention is to provide monomers to be used in preparation of an affinity material of the present invention.

One object of the present invention is achieved by a molecularly imprinted polymer, wherein said polymer is cross-linked and comprises one or more sites selectively binding one or more antibodies, wherein said one or more sites are complementary to one or more template molecule selected from one or more peptides comprising an amino acid sequence corresponding to a contiguous or non-contiguous subsequence of a domain of one or more antibodies.

One object of the present invention is achieved by a molecularly imprinted polymer, obtainable by providing one or more monomers, template molecules, initiators and cross-linking agents; polymerizing said one or more monomers, templates, initiators and cross-linking agents; removing said templates; wherein said one or more template molecules is independently selected from one or more peptides comprising an amino acid sequence corresponding to a subsequence of a domain of one or more antibodies.

One object of the present invention is achieved by a molecularly imprinted polymer obtained as described above and where the monomer is selected from:

One object of the present invention is achieved by using any of the monomers above in the preparation of molecularly imprinted polymers.

One object of the present invention is achieved by a method for purifying an antibody, wherein said antibody is contacted by a molecularly imprinted polymer according to the invention and as disclosed in the accompanying claims.

DETAILED DESCRIPTION OF THE FIGURES

DETAILED DESCRIPTION OF THE PRESENT INVENTION

The present invention relates robust, low cost affinity materials useful in antibody purification. The affinity material is based on molecularly imprinted polymers, and in some embodiments the affinity material is made of molecularly imprinted polymers.

Molecular imprinting has so far resulted in a range of "tailor-made" receptors in the form of molecularly imprinted polymers (MIPs), designed predominantly for binding small, lipophilic target molecules. Production of MIPs entails polymerization of mono- and polyfunctional monomers in the presence of a template. After removal of the template imprinted sites are revealed that can be reoccupied by the template or a closely related compound, such as a compound incorporating the template as a sub-chemical moiety or a compound related to the template. In the application of this technology to proteins, the sub-chemical moiety would be an 'epitope' of the protein comprising a certain number of amino acids taken from the protein. The epitope may be formed from contiguous, or non-contiguous but spatially close, amino acid sequences. Non-limiting examples thereof are molecularly imprinted polymers imprinted with an epitope (template) of a protein, such as an antibody, comprising sites that can recognize proteins containing the epitope.

Vis-á-vis biological receptors, MIPs are distinguished by robustness and ease of preparation, which has led to their implementation in numerous molecular recognition based applications targeting small molecules. While MIPs have proven their value for the enrichment of low molecular weight analytes, they have had little success in enriching biological macromolecules.

Figure 2:
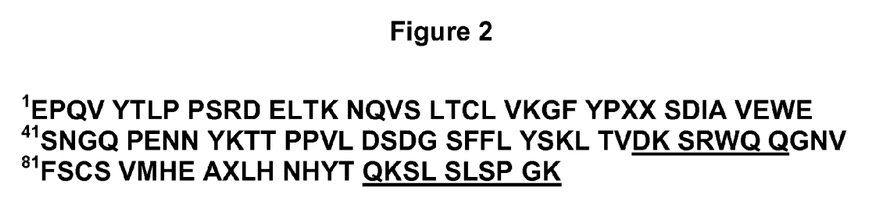
FIG. 2 discloses the sequence of the CH3 domain of an immunoglobulin G heavy chain. The C-terminal sequence (QKSLSLSPGK) indicated in the specification as a potential—'C-terminal template' is underscored. The internal sequence (DKSRWQQ) suggested as a 'continuous epitope' in the specification is also underscored. The numbering used is an arbitrary scheme and the internal sequence represents amino acid numbers 71 to 77. X indicates an unknown amino acid.

In one embodiment of the present invention a molecularly imprinted polymer is characterized as a cross-linked polymer comprising one or more sites selectively binding one or more antibodies, wherein said one or more sites are complementary to one or more template molecules selected from one or more peptides comprising an amino acid sequence corresponding to a subsequence of a domain of one or more antibodies. In one embodiment the domain is an immunoglobulin G heavy chain constant domain. A sub-sequence of said constant domain could for example be represented by the following C-terminal epitopes: QKSLSLSPGK, QKSLSLSPG, QKSLSLSP, QKSLSLS, QKSLSL, QKSLS, QKSL etc. (see FIG. 2). The following sub-sequences from the C-terminal could also be used: QKSLSLSPGK, KSLSLSPGK, SLSLSPGK, LSLSPGK, SLSPGK, LSPGK, SPGK, PGK and GK.

During the polymerization step in the preparation of the molecularly imprinted polymer, the monomers are interacting with the template molecules through electrostatic, hydrophobic or other interactions leading to the formation of binding sites in the polymer that are complementary to the template molecules. Complementary in this sense means that the interacting groups in the polymer are placed such that they are in a good position to interact with the interacting groups in the template molecule and other molecules that contain the template molecule as a substructure, in this case an antibody which contains the template sequence as an epitope, for example the C-terminal. This arrangement of interacting groups in a specific way also leads to selective binding as the arrangement is less suitable to bind other amino acid sequences compared to the sequence that was used as the template. The polymer will consequently bind the target amino acid sequence selectively, i.e. bind to it stronger than it will bind to other amino acid sequences.

In a further embodiment, the domain is an immunoglobulin G heavy chain constant domain where epitope sequences are used comprising amino acids that are spatially close but may be distant in sequence. Such 'discontinuous epitopes' may be represented by a linear sequence of amino acids. For example, in the following imaginary sequence:

```
A G K L L W Y R A I H S T L L I Y R A F A F W
1 2 3 4 5 6 7 8 9 0 1 2 3 4 5 6 7 8 9 0 1 2 3
```

Let us suppose that residues 3, 7, 8, 11, 12, 17 & 18 are known to be surface located and spatially close. In the present invention, such an epitope can be represented by the linear sequence:

```
K Y R H S Y R
```

In a further embodiment, the domain is an immunoglobulin G heavy chain constant domain where epitope sequences are used comprising amino acids that are contiguous in sequence, exposed at the surface of the immunoglobulin but are neither at the C-terminus nor the N-terminus of the immunoglobulin chain. Such 'continuous epitopes' typically comprise amino acid sequences that 'loop' out from the surface of the immunoglobulin and hence are exposed to the aqueous environment. They may be represented by a linear sequence of amino acids in a short (in this instance, 7 amino acids) peptide. For example, the following sample sequence:

D K S R W Q Q represents amino acid numbers 71 to 77 (see FIG. 2); arbitrary numbering; of the immunoglobulin G constant domain. These amino acids are present in a loop structure and are contiguous amino acids which when present as a 7 amino acid peptide bearing this sequence would act as a continuous epitope according to the present invention.

Such linear sequences as illustrated above can be used as epitope templates in the present invention. The specificity site created within the molecularly imprinted polymer by the use of such templates may be expected to exhibit cross-reactivity with the same region of sequence when embedded within the natural immunoglobulin. In some ways this is analogous to the successful use of linear peptides as antigens in eliciting a cross-reactive response to intact proteins during generation of an in vivo immune response (see van Oss & Regenmortel, Eds. Immunochemistry, Marcel Dekker, 1994).

In one embodiment of the present invention the molecularly imprinted polymer is obtained by providing one or more monomers, templates, and initiators;

polymerizing said one or more monomers, templates, and initiators; removing said templates; wherein said polymer said one or more templates are independently selected from one or more peptides comprising an amino acid sequence corresponding to a subsequence of a domain of one or more antibodies. In some embodiments cross-linking agents are provided together with said one or more monomers, templates, and initiators and in some embodiments said one or more monomers may function as a combined monomer and cross-linking agent.

In one embodiment the monomers used in the present invention are 1-10. In one embodiment of the present invention the monomer is selected from monomer 1 or 9.

In one embodiment of the present invention epitope and interfacial imprinting concepts are used for the development of affinity material used in the capturing step in antibody production.

In one embodiment of the present invention epitopes are used for the development of affinity material used in the capturing step in antibody production. In some embodiments said affinity material is based on molecularly imprinted polymers.

The initiator may be an azo initiator such as 2,2'-azobis(2-methylpropionitrile) (AIBN) or 2,2'-azobis(2,4-dimethylvaleronitrile) (ABDV), a peroxide iniator such as benzoyl peroxide or tert-butyl peroxide, a persulfate initiator such as ammonium persulfate or potassium persulfate or any other radical initiator known to the skilled person. N,N,N',N'-tetramethylethylenediamine (TMEDA) may be added as an accelerator. Polymerization may be initiated thermally or by irradiation with UV light.

Epitope imprinting is a bio-inspired approach making use of a peptide comprising one or more amino acid sequences as templates corresponding to an exposed domain found on the surface of the target protein (commonly N- or C-terminal but may be in other locations also). When imprinted, epitopes as templates result in surface-confined binding sites complementary to the epitope. The resulting material is capable of recognizing larger peptides or whole proteins containing the epitope sequence.

Antibodies are for example IgA, IgD, IgE, IgG and IgM.

In one embodiment of the present invention the molecularly imprinted polymer comprises one or more sites that are complementary to one or more template molecules selected from one or more peptides comprising an amino acid sequence corresponding to a subsequence of a domain of one or more antibodies.

In one embodiment two paths differing with respect to the step in the downstream process in which the material will be implemented. Thus cost-efficient capturing phases exhibiting enhanced affinity, capacity and robustness for IgG (antibody) will be developed based on imprinting techniques using epitopes as templates.

The affinity materials (molecularly imprinted polymer) is implemented in the downstream processing in the production of antibodies.

Epitope imprinting of IgG or any other antibody can be performed using a set of novel functional monomers based on methacrylamides. Other, selective functional monomers operating in a host-guest manner and referred to as host monomers, may for example bind to one specific class of amino acid side chains which are frequently exposed on protein surfaces, for example monomers 1, 3, 7 and 9. (Renner C., Piehler J., Schrader T., Arginine and Lysine Specific Polymers for Protein Recognition and Immobilization, J. Am. Chem. Soc., 2006, 128, 620-628.) This series of polymerizable binding sites can be used to develop imprinted polymers for capturing antibodies. To be useful as a generic capture method, epitopes from constant domains in antibodies should be targeted and imprinted in this way. For example, the C-terminal penta-decapeptide fragments from the immunoglobulin G heavy (gamma) chain may used as templates for imprinting by radical copolymerization with appropriate amounts of water-soluble crosslinkers in the presence of selected key functional monomers (1-10 shown below).

9

10

The above mentioned monomers may successfully be used in the present invention. The preparation of monomers 2, 5 and 6 has previously been disclosed by Schrader et al in Chemistry, Eur. J. 2007, 13, 7701-7707.

The preparation of monomer 3 has previously been disclosed by C. Renner, J. Piehler, T. Schrader, J. Am. Chem. Soc., 2006, 128, 620-628.

The preparation of monomer 4 has previously been disclosed by Taden, A. H. Tait, A. Kraft, J. Polym. Sci., Polym. Chem., 2002, 40, 4333-4343.

The preparation of monomer 7 has previously been disclosed by B. R. Hart, K. J. Shea, Macromolecules, 2002, 35, 6192-6201.

The preparation of monomer 10 has previously been disclosed by J. H. G Steinke et al Trends in Analytical Chemistry vol 18(3), 1999, p. 159.

In some embodiments of the present invention conventional functional monomers such as methacrylamide, acrylamide, methacrylic acid, acrylic acid, 2-vinylpyridine, 4-vinylpyridine, itaconic acid, 2-acrylamido-2-methylpropanesulfonic acid, 2-(trifluoromethyl)acrylic acid, 1-vinyl imidazole, 2-hydroxyethyl methacrylate, 4-vinylbenzoic acid, N,N-diethylaminoethyl methacrylate, allylamine or 1-vinyl-2-pyrrolidone are used in the preparation of the molecular imprinted polymer.

In some embodiments of the present invention cross-linking agents, such as ethylene glycol dimethacrylate, trimethylolpropane, divinylbenzene. pentaerythritol trimethacrylate, N,N'-methylenebisacrylamide, N,N'-ethylenebisacrylamide, poly(ethylene glycol) methacrylate or dimethacrylate containing 2-1000 ethylene glycol units are used in the preparation of the molecular imprinted polymer.

In one embodiment of the present invention the template peptide may be attached to a PEG chain (polyethylene glycol) where the PEG mimics the remainder of the antibody 'bulk' during the polymerization process. Alternatively, the template may be attached to, or synthesized on a disposable support, such porous silica. In the latter case, the disposable support is removed after polymerization by dissolution under alkaline conditions.

In one embodiment the molecularly imprinted polymer is grafted to a non-disposable support, such as wide pore silica, controlled pore glass and non-porous silica and polymeric supports.

EXAMPLES

Example 1

Preparation of Monomer 1

3,5-diaminomethyl nitrobenzene 3,5-dibromomethyl nitrobenzene (6.00 g, 19.4 mmol) and sodium azide (2.91 g, 44.7 mmol) were dissolved in 200 ml DMF and refluxed overnight. After the solvent was removed, the crude product was dissolved in 200 ml $CH_2Cl_2$ and washed with 50 ml water for 5 times. The organic phase was dried over $MgSO_4$ and the solvent was distilled off. The crude was dissolved in 150 ml THF and triphenylphosphine (10.0 g, 40.8 mmol) was added slowly at 0° C. After the mixture was stirred overnight at room temperature, water was added and the mixture was kept stirring for another 10 minutes. Aqueous phase was acidified with acetic acid to PH=2, and washed with $CH_2Cl_2$. Then it was basified to PH=10 and extracted with $CH_2Cl_2$. The solvent was distilled to give the title compound (2.90 g, 83%).

3,5-bis-(N,N'-bis-Boc-guanidinyl)methyl nitrobenzene 3,5-diaminomethyl-nitrobenzene (1.40 g, 7.73 mmol), N,N'-bis-Boc-2-methylthiourea (4.48 g, 14.7 mmol), triethylamine (2.00 ml, 15.1 mmol) and silver nitrate (2.50 g, 14.7 mmol) were dissolved/suspended in 100 mL $CH_2Cl_2$. The mixture was stirred for 5 days at room temperature. During this period the colour changed from yellow to dark brown. The precipitation was filtered and the solvent was removed. The crude product was chromatographied over silica gel with ethyl acetate ester and hexane as the eluent (1:3, $R_f$=0.3) to give the title compound (720 mg, 14%).

3,5-bis-(N,N'-bis-Boc-guanidinyl)methyl aniline

3,5-bis-(N,N'-bis-Boc-guanidinyl)methyl nitrobenzene (4.52 g, 6.86 mmol) was dissolved in 50 ml absolute methanol, and catalytic amount of Pd/C was added into this mixture. The mixture was stirred at room temperature under hydrogen atmosphere for four hours. The solvent was removed to give the title compound as a light yellow solid (100%).

3,5-bis-(N,N'-bis-Boc-guanidinyl)methylphenyl-methacrylamide 3,5-bis-(N,N'-bis-Boc-guanidinyl)methyl aniline (4.00 g, 6.29 mmol) and triethylamine (1.75 ml, 12.6 mmol) were dissolved in 100 mL $CH_2Cl_2$, and methylacroyl chloride (1.22 ml, 12.6 mmol) in 50 ml $CH_2Cl_2$ was added dropwisely at 0° C. After the addition, the mixture was stirred for three hours and the solvent was removed. The product was chromatographied over silica gel (ethyl acetate ester: hexane 3:1, $R_f$=0.2) to give the title compound as a white solid (3 g, 76%).

3,5-(bis-guanidinium-methyl)phenylmethacrylamide hydrochloride 3,5-bis-(N,N'-bis-Boc-guanidinyl)methyl phenyl-methacrylamide (4.00 g, 4.27 mmol) was dissolved in 50 mL $CH_2Cl_2$ and 50 ml 2 M HCl in diethyl ether was added. The mixture was stirred overnight. The precipitation was filtered and dried in vacuum to give the title compound as a light yellow viscous solid (1.4 g, 100%).

Example 2

Preparation of Monomer 9

6'-Deoxy-6'-N-(2-aminoethylamino)-β-cyclodextrin

6'-o-(p-Tolylsulfonyl)-β-cyclodextrin (200 mg, 155 mol) was dissolved in ethylene diamine (1.03 ml, 15.5 mmol) and the mixture was refluxed at 70° C. under argon atmosphere overnight. After the excess amine was distilled, 10 ml ethanol was added and the mixture was refluxed for another 30 min. The precipitation was filtered and dissolved in 10 ml water. The aqueous solution was washed with 10 ml dichloromethane for three times and flowingly condensed to about 0.5 ml. Ethanol was added dropwise to precipitate a white product, which was further washed with hexane to give the title compound (131 mg, 72%).

6'-Deoxy-6'-(N-(2-methacrylamidyl)ethylamino)-β-cyclodextrin

6'-Deoxy-6'-N-(2-aminoethylimino)-β-cyclodextrin (1.00 g, 850 umol) and triethylamine (0.14 ml, 1.02 mmol) were dissolved in 50 ml DMF. To this solution methylacroyl chloride (1.81 ml, 1.87 mmol) in 10 ml DMF was added dropwise at 0° C. The mixture was stirred overnight and DMF was distilled under vacuum. The solid was dissolved in 1 ml water and precipitated with 10 ml ethanol. If the precipitation was too fine, some hexane could be added. The white solid was filtered and dried to give the title compound (529 mg, 50%).

Example 3

Synthesis of PEG Derivatized Epitope Template and Use for Preparing an Epitope Imprinted Polymer The peptide corresponding to the constant IgG C-terminal sequence QKSLSLSPGK, DDE (N-1-(4,4-dimethyl-2,6-dioxycyclohexylidene) protected at the amino acid side chains of K and the C-terminus protected as a t-butyl ester (obtainable through custom peptide synthesis by many different peptide suppliers), was reacted at the N-terminus with Methoxy PEG Succinimidyl Carboxymethyl ester MW-5000. The protecting groups were cleaved off. The conjugate was used as template in molecular imprinting.

5% Crosslinked gels: N,N'-Ethylenebis(acrylamide) (1 mmol) and acrylamide (19 mmol) were dissolved in distilled, deionized and deoxygenated water. To this solution the template (0.02 mol) described above was added, followed by a solution of TMEDA (N,N,N',N'-tetramethylethylenediamine) and ammonium persulfate (1% w/w) in $H_2O$. After purging with nitrogen gas, the reaction container was closed and subsequently heated to 35° C. for 24 h. The gel was washed with acidified water to remove the template and followed by water until neutral pH was obtained.

30% Crosslinked gels: N,N'-Ethylenebis(acrylamide) (6 mmol) and acrylamide (14 mmol) were dissolved in distilled, deionized and deoxygenated water. To this solution was added the template (0.02 mol) described above followed by a solution of TMEDA and ammonium persulfate (1% w/w) in $H_2O$. After purging with nitrogen gas, the reaction container was closed and subsequently heated to 35° C. for 24 h. The gel was washed with acidified water to remove the template and followed by water until neutral pH was obtained.

Example 4

Immobilized Imprinting of a C-Terminal Epitope

Silica (Si500, Pore volume: 0.78 cc/g, Pore Diameter: 50 nm, Surface area: 58 m²/g, particle size 5 μm) was activated by heating to reflux in 17% HCl overnight and then modified with 3-aminopropyl(trimethoxysilane) (APS) followed by acylation with succinic anhydride to give silica containing free carboxylic acid groups. Thereafter the protected (side chains of K and C-terminus) peptide corresponding to the IgG C-terminal epitope as described in Example 3 was immobilized on the silica by PyClOP (chlorotripyrrolidinophosphonium hexafluorophosphate) mediated coupling. The protecting groups were cleaved off and the resulting peptide modified silica was used as a template for molecular imprinting as follows.

A polymerization solution was prepared by mixing a monomer, acrylamide (19 mmol); a cross-linker, N,N'-methylene bisacrylamide (MBA, 1 mmol); an initiator, ammonium persulfate (APS, 5 mg); an accelerator, TMEDA, 5 μl; and a porogenic solvent, dimethylformamide (DMF, 0.7 ml). Thereafter, the following steps were performed: the remaining wash solution was removed from the pores via $N_2$ flow; the $N_2$ gas was removed from the pores by vacuum; the polymerization solution was injected to the silica-peptide particles; the silica-peptide particles were washed with isooctane; polymerizing at 37° C.; the resulting composite particles was etched with $NH_4HF_2$, 3M, to remove the silica; the samples were washed with water and methanol; and the obtained polymer particles were dried under vacuum at 60° C. overnight.

Example 5

Immobilized Imprinting of a an Internal Continuous Epitope

Silica (Si500, Pore volume: 0.78 cc/g, Pore Diameter: 50 nm, Surface area: 58 m²/g, particle size 5 μm) was activated by heating to reflux in 17% HCl overnight and then modified with 3-aminopropyl(trimethoxysilane) (APS) followed by acylation with succinic anhydride to give silica containing free carboxylic acid groups. Thereafter the protected (side chains of D and K and N- and C-terminus) peptide from the IgG-internal epitope corresponding to residues 92 to 98 of the immunoglobulin G heavy chain (DKSRWQQ) was immobilized on the silica by PyClOP mediated coupling. The protecting groups were cleaved off. The peptide modified silica was used for imprinting according to the procedure of Example 4.

Example 6

Immobilized imprinting of a C-terminal epitope using monomer 2, 4, 5, 6 or 10. Same as Example 4, but with a polymerization solution prepared by mixing a monomer, monomer 2, 4, 5, 6 or 10 (4 mmol); a second monomer, acrylamide (15 mmol); a cross-linker, N,N'-methylenebisacrylamide (MBA, 1 mmol); an initiator, ammonium persulfate (APS, 5 mg); an accelerator, TMEDA, 5 μl; and a porogenic solvent, N,N'-dimethylformamide, DMF (1.2 mL).

Example 7

Immobilized imprinting of a C-terminal epitope using host-monomer 1, 3, 7 or 9. Same as Example 4, but with a polymerization solution prepared by mixing a host-monomer, monomer 1, 3, 7 or 9 (1 mmol); a second monomer, acrylamide (18 mmol); a cross-linker, N,N'-ethylenebisacrylamide (EBA, 1 mmol); an initiator, ammonium persulfate (APS, 5 mg); an accelerator, TMEDA, 5 µl; and a porogenic solvent, 50 mM phosphate buffer pH 7 (1.2 mL).

Example 8

Immobilized Imprinting of a C-Terminal Using Methacrylic Acid 100 g 1000 Å silica (surface area 29 m²/g, pore volume 0.71 cc/g, particle size 40-75 µm) was refluxed in a solution of 90 mg 3-aminopropyl(triethoxysilane) in 1 L of toluene overnight. The silica was filtered off, washed twice with toluene and twice with methanol and then dried. Silica containing 3.7 µmol/g (0.13 µmol/m²) 3-aminopropyl groups was obtained.

The silica was added to a solution of 0.74 g succinic anhydride in 500 mL 1-methyl-2-pyrrolidone and shaken overnight. 0.76 g of acetic anhydride was added and the mixture was shaken overnight again. The silica was filtered off, washed twice with water and twice with methanol and then dried. Silica containing approximately 3.7 µmol/g (0.13 µmol/m²) carboxylic acid groups was obtained.

The silica was suspended in 300 mL 1-methyl-2-pyrrolidone dried over 4 Å molecular sieves. 1.36 g pentafluorophenol and 0.93 g N,N'-diisopropylcarbodiimide were added and the mixture was shaken overnight. The silica was filtered off, washed twice with 1-methyl-2-pyrrolidone and twice with acetonitrile and then dried.

444 µmol of the protected amino acid sequence Gln-Lys (Dde)-Ser-Leu-Ser-Leu-Ser-Pro-Gly-Lys(Dde) (obtainable through custom peptide synthesis by many different peptide suppliers) corresponding to the constant IgG C-terminal was dissolved in 300 mL 1-methyl-2-pyrrolidone dried over 4 Å molecular sieves and 60 mg 1-hydroxybenzotriazole and 143 mg of N,N'-diisopropylethylamine were added. The silica was added to the solution and the mixture was shaken overnight. The silica was filtered off, washed once with 1-methyl-2-pyrrolidone, twice with water and twice with acetonitrile and then dried.

The silica was suspended in 300 mL N,N'-dimethylformamide, 6 mL hydrazine hydrate was added and the mixture was shaken for 1 h. The silica was filtered off, washed twice with N,N'-dimethylformamide and three times acetonitrile and then dried. Silica with immobilized C-terminal epitope was obtained.

497 mg 2,2'-azobis(2,4-dimethylvaleronitrile) was dissolved in a mixture of 19.8 g ethylene glycol dimethacrylate and 1.72 g methacrylic acid. 10.5 mL of the mixture was added to 15 g of the silica with immobilized C-terminal epitope in three equal portions with stirring until free-flowing after each addition. The monomer-containing silica was subjected to three vacuum/nitrogen cycles and then heated to 50° C. for 24 h. The silica was transferred to a plastic container, 540 mL of 3M $NH_4HF_2$ solution was added and the mixture shaken for three days to remove the silica. The polymer was filtered off, washed with warm water, methanol and then dried. The polymer was washed with formic acid at 95° C., methanol and dried.

Example 9

Purification of Antibodies Using the MIP 1 mL of a fermentation broth containing 1 mg/mL of IgG is passed through a column containing 25 mg of the molecularly imprinted material from Example 3, 4, 5, 6, 7 or 8. The IgG is retained in the column. The column is then washed three times with 1 mL 0.01 M phosphate buffered saline, pH 7.2. The IgG is retained in the column. The column is washed with 1 mL distilled water containing 1% formic acid and 20% isopropanol. Purified IgG is released from the column and the solution is lyophilized to obtain purified IgG.

Example 10

Purification of Monoclonal Antibodies Using the MIP

30 L of cell free culture supernatant containing monoclonal antibody (approx 50 mg/L) is passed through a column (bed height 8 cm; column volume 150 mL) packed with MIP particles from Examples 3-8, at a flow rate of approx 80 mL/min. The column is thereafter washed with ca 2 L of Tris/HCl buffer (50 mM, pH 8.0) followed by an elution step using sodium citrate buffer (150 mM) at pH 2-3. After neutralization and lyophilization 3.5 g of purified (ca 95% purity) antibody is obtained.

The invention claimed is:

1. A molecularly imprinted polymer, wherein said polymer is cross-linked and comprises one or more sites selectively binding one or more antibodies, wherein said one or more sites are complementary to one or more template molecule selected from one or more peptides comprising an amino acid sequence corresponding to a subsequence of a domain of one or more antibodies wherein said amino acid sequence is selected from the group consisting of QKSLSLSPGK, QKSLSLSPG, QKSLSLSP, QKSLSLS, QKSLSL, QKSLS, QKSL, QKS, QK KSLSLSPGK, SLSLSPGK, LSLSPGK, SLSPGK, LSPGK, SPGK, PGK or GK.

2. A molecularly imprinted polymer, obtainable by
   providing one or more monomers, template molecules, initiators and cross-linking agents;
   polymerizing said one or more monomers, templates, initiators and cross-linking agents;
   removing said templates;
wherein said one or more template molecules is independently selected from one or more peptides comprising an amino acid sequence corresponding to a subsequence of a domain of one or more antibodies wherein said amino acid sequence is selected from the group consisting of QKSLSLSPGK, QKSLSLSPG, QKSLSLSP, QKSLSLS, QKSLSL, QKSLS, QKSL, QKS, QK KSLSLSPGK, SLSLSPGK, LSLSPGK, SLSPGK, LSPGK, SPGK, PGK or GK.

3. A molecularly imprinted polymer according to any one of claims 1-2 wherein said amino acid sequence is QKSLSLSPGK.

4. A molecularly imprinted polymer according to any one of claims 1-2, wherein the one or more template molecules are attached to a disposable support material or a polymer chain.

5. A molecularly imprinted polymer according to claim 4, wherein the disposable support material is silica and the polymer chain is a polyethylene glycol chain.

6. A molecularly imprinted polymer according to claim 2, wherein the monomer is a host-monomer capable of binding an amino acid side chain.

7. A molecularly imprinted polymer according to claim 6, wherein the host-monomer is selected from:

8. A molecularly imprinted polymer according to claim 7, wherein the host-monomer is selected from:

9. A molecularly imprinted polymer according to claim 2, wherein the monomer is selected from:

10. A molecularly imprinted polymer according to any one of claims 1-2, wherein the molecularly imprinted polymer is grafted to a non-disposable support material.

11. A molecularly imprinted polymer according to claim 10, wherein the non-disposable support material is selected from wide pore silica, controlled pore glass and non-porous silica and polymeric supports.

12. A method for purifying an antibody, wherein said antibody is contacted by a molecularly imprinted polymer according to any one of claims 1-2.

\* \* \* \* \*

UNITED STATES PATENT AND TRADEMARK OFFICE
CERTIFICATE OF CORRECTION

| | | |
|---|---|---|
| PATENT NO. | : 8,569,451 B2 | Page 1 of 1 |
| APPLICATION NO. | : 13/263954 | |
| DATED | : October 29, 2013 | |
| INVENTOR(S) | : Rees et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 67 days.

Signed and Sealed this
Fourth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,569,451 B2                                                 Page 1 of 1
APPLICATION NO.    : 13/263954
DATED              : October 29, 2013
INVENTOR(S)        : Rees et al.

It is certified that error appears in the above-identified patent and that said Letters Patent is hereby corrected as shown below:

In the Claims

Column 16, line 28, in Claim 1, delete "molecule" and insert --molecules--, therefor Column 16, line 41, in Claim 2, after "agents;", insert --and--, therefor Signed and Sealed this
Twelfth Day of August, 2014

Michelle K. Lee
*Deputy Director of the United States Patent and Trademark Office*